US00PP11656P

United States Patent [19]

Kotobuki et al.

[11] Patent Number: Plant 11,656

[45] Date of Patent: Nov. 28, 2000

[54] JAPANESE PEAR TREE NAMED 'OSA GOLD'

[75] Inventors: Kazuo Kotobuki, Tsukuba; Tetsuro Sanada; Tetsuo Masuda, both of Morioka; Toji Yoshioka, Naka-gun; Minoru Nagara, Kurayoshi; Masato Uchida, Yazu-gun; Kosuke Inoue, Tottori; Kenji Murata, Yazu-gun; Kenichi Kitagawa; Akira Yoshida, both of Tottori, all of Japan

[73] Assignee: National Institute of Agrobiological Resources Ministry of Agriculture, Forestry and Fisheries, Tsukuba, Japan

[21] Appl. No.: 09/114,484

[22] Filed: Jul. 13, 1998

[51] Int. Cl.[7] ..... A01H 5/00

[52] U.S. Cl. ..... Plt./178

[58] Field of Search ..... Plt./178

[56] References Cited

U.S. PATENT DOCUMENTS

P.P. 8,529 1/1994 Nishida et al. ..... Plt./178
P.P. 9,835 3/1997 Spira et al. ..... Plt./178

OTHER PUBLICATIONS

UPOV–ROM GTITM Computer Database 1999/02 GTI Jouve retrieval Softward, Citation for 'Osa Gold', Mar. 29, 1999.

"New Japanese Pear Cultivar 'Kotobuki Shinsui'—A Mutant resistant to the Black Spot Disease of Japanese Pear", Masuda et al. Technical News No. 57 Institute of Radiation Breeding, Mar. 1997.

"'Gold Nijisseiki', a new Japanese Pear Mutant Cultivar Resistant to Black Spot Disease Induced by Chronic Irradiation of Gamma–Rays", Kotobuki et al, *Bulletin of the National Institute of Agrobiological Resources*, Mar. 1992, pp. 105–120.

*Primary Examiner*—Howard J. Locker
*Assistant Examiner*—Wendy A Baker
*Attorney, Agent, or Firm*—Arent Fox Kintner Plotkin & Kahn, PLLC

[57] ABSTRACT

The new and distinct cultivar relates to a Japanese pear tree that has a strong resistance to black spot disease and has substantially the same excellent qualities of 'Osanijisseki' as a Japanese pear cultivar. This pear tree is self-compatible and bears a yellowish green fruit, is moderately sweet and acidic, and has a good taste that is suitable for a dessert pear.

11 Drawing Sheets

BACKGROUND OF THE CULTIVAR

The present invention relates to a new and distinct cultivar of a Japanese pear tree (*Pyrus pyrifolia*), and, particularly, to a tree bearing fruits with a yellowish-green skin, having charateristics substantially the same as those of 'Osanijisseiki' (unpatented in the United States) but having a significantly strong resistance to black spot disease.

'Osanijisseiki', which was discovered as a self-compatible spontaneous bud sport of the Japanese pear 'Nijisseiki' and was released in 1979, has substantially the same characteristics as those of 'Nijisseiki' except that 'Osanijisseiki' is self-compatible. It has, however, a shortcoming in that 'Osanijisseiki' has a high susceptibility to black spot disease, as does 'Nijisseiki'. Black spot disease is one of the most important diseases of susceptible varieties, such as 'Nijisseiki' and 'Osanijisseiki', and a great deal of labor is required to control it. A new cultivar of the pear fruit tree having a strong resistance to black spot disease, while also having the excellent characteristics of 'Osanijisseiki' has been required for a long time.

The object of the present invention is to obtain a resistant mutant cultivar of the pear fruit tree, having a strong resistance to black spot disease while also having the excellent characteristics of 'Osanijisseiki', using irradiation of γ-rays.

ORIGIN AND ASEXUAL REPRODUCTION OF THE CULTIVAR

The new cultivar of a Japanese pear tree was derived from 'Osanijisseki' by mutation breeding.

The Institute of Radiation Breeding, National Institute of Agrobiological Resources, Ministry of Agriculture, Forestry and Fisheries, in cooperation with Tottori Horticultural Experiment Station has carried out collaborative research on radiation breeding for selection of resistant mutants to the black spot disease in the Japanese pear 'Osanijisseiki'.

In 1986, young trees of the Japanese pear cultivar 'Osanijisseiki', were planted in the Gamma Field at a position 40–70 meters (10-meter intervals) from the $^{60}$Co source. The selection of resistant mutants to black spot disease had been performed since 1986 using crude AK toxin. In the summer of 1991, a mutated twig of 'Osanijisseiki' having resistance to black spot disease was selected on a young tree at 40 meters from the $^{60}$Co source. This mutated twig, having distinctively stronger resistance to the black spot disease than the original cultivar, was grafted on a seedling rootstock outside of the Gamma Field to study its characteristics such as vigor while confirming the disease resistance of the twig using crude toxin of the black spot disease. In spring of 1992, propagated twigs were top-grafted on mature Japanese pear trees of unknown parentage using 'Suisei' (unpatented in the United States) as interstocks.

As the trees bore fruits for the first time in 1993, self-compatibility and fruit characteristics were studied. Since then, it has been found that the trees have a significantly strong resistance to black spot disease compared to 'Osanijisseiki' while also displaying the excellent characteristics of 'Osanijisseiki'.

This new and distinct cultivar of Japanese pear tree was asexually propagated by grafting, at the Institute of Radiation Breeding, NIAR, Ohmiya-machi, Naka-gun, Ibaraki-ken, Japan and the homogeneity and stability thereof were confirmed. The new cultivar was named 'OSA GOLD'.

SUMMARY OF THE CULTIVAR

The characteristics of the new cultivar of the Japanese pear tree 'OSA GOLD' are substantially the same as those of 'Osanijisseiki', except that the present 'OSA GOLD' has an obviously stronger resistance to black spot disease than that of the original cultivar and the new cultivar can be cultivated under the same control as 'Kosui' (unpatented in the United States) or 'Hosui' (unpatented in the United States) which are resistant to black spot disease.

The new cultivar is regular bearing and has a strong vigor, light greenish brown shoots, few axillary flower buds, many spurs and a high quality fruit.

Flowering time is a little earlier than that of 'Kosui' i.e. from the middle to the end of April in Ibaraki Prefecture in Japan. The flowers have fewer petals than those of 'Kosui' and the color of anther is deep red and deeper than that of 'Kosui'.

The new cultivar is highly self-compatible, as is the original cultivar, and forms many seeds upon self-pollination.

The tree produces a round-shaped fruit that matures in the middle of September in Ibaraki Prefecture in Japan.

Though the fruit has a rather small size at first or second fruiting, (i.e., about 270 g), the average size will be about 300–350 g like that of the original cultivar.

The fruit has a yellowish green skin and the extent of occurrence of russet is medium in unbagged fruit.

The flesh is yellowish white and is more yellowish than that of 'Kosui' in color, and slightly softer and finer than that of 'Kosui'.

The sugar content is about 11–12% and lower than that of 'Kosui'.

DESCRIPTION OF THE CULTIVAR

Figure 1:
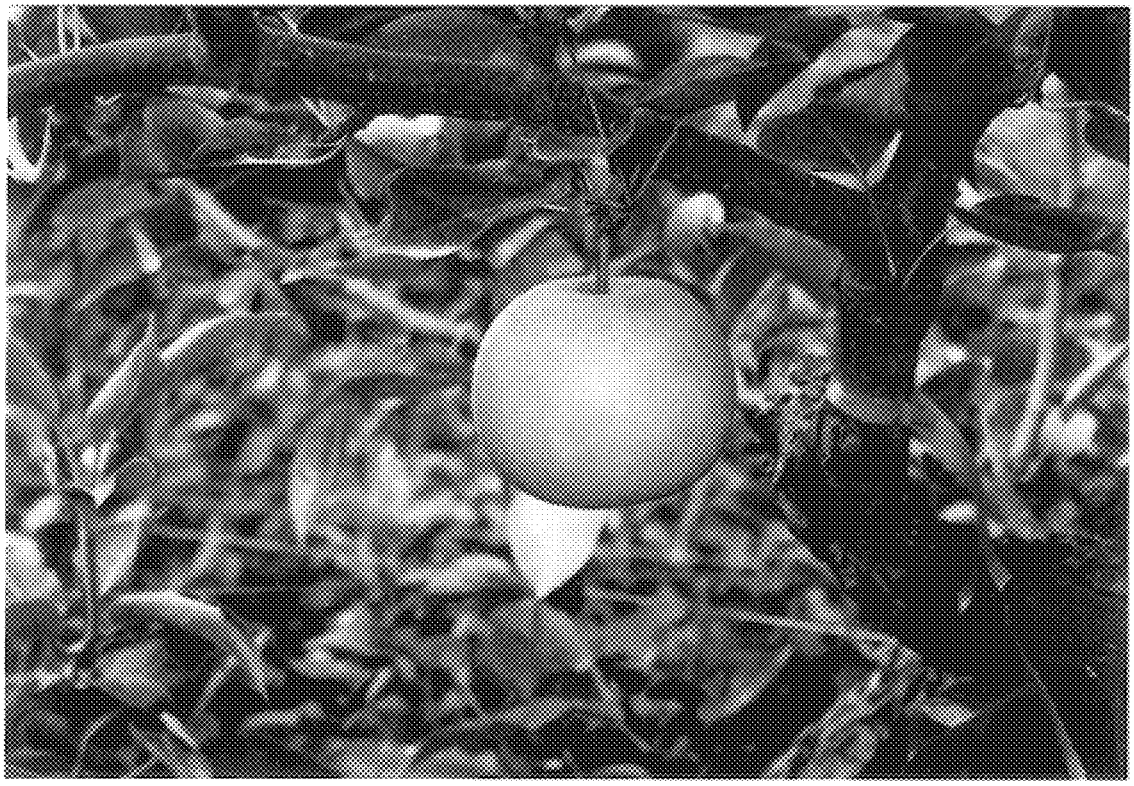
FIG. 1 is a photograph of a fruit bearing shoot of the new cultivar of Japanese pear tree.
Figure 2:
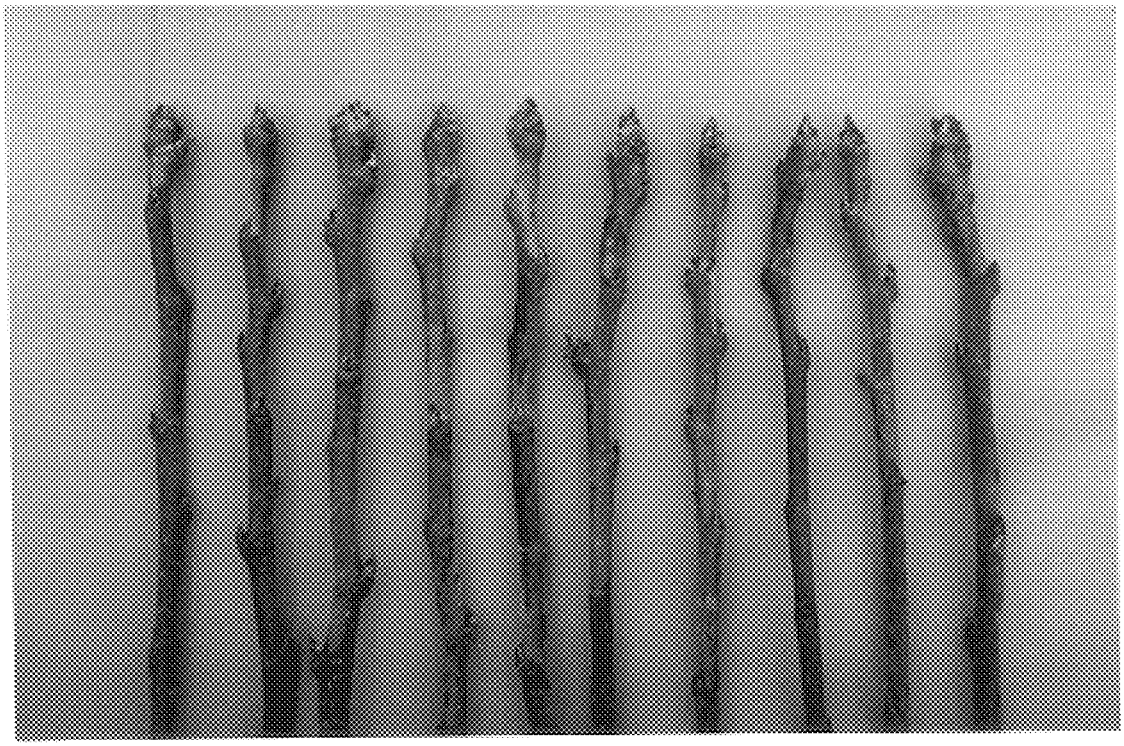
FIG. 2 is a photograph of branches of the new cultivar of Japanese pear tree.
Figure 3:
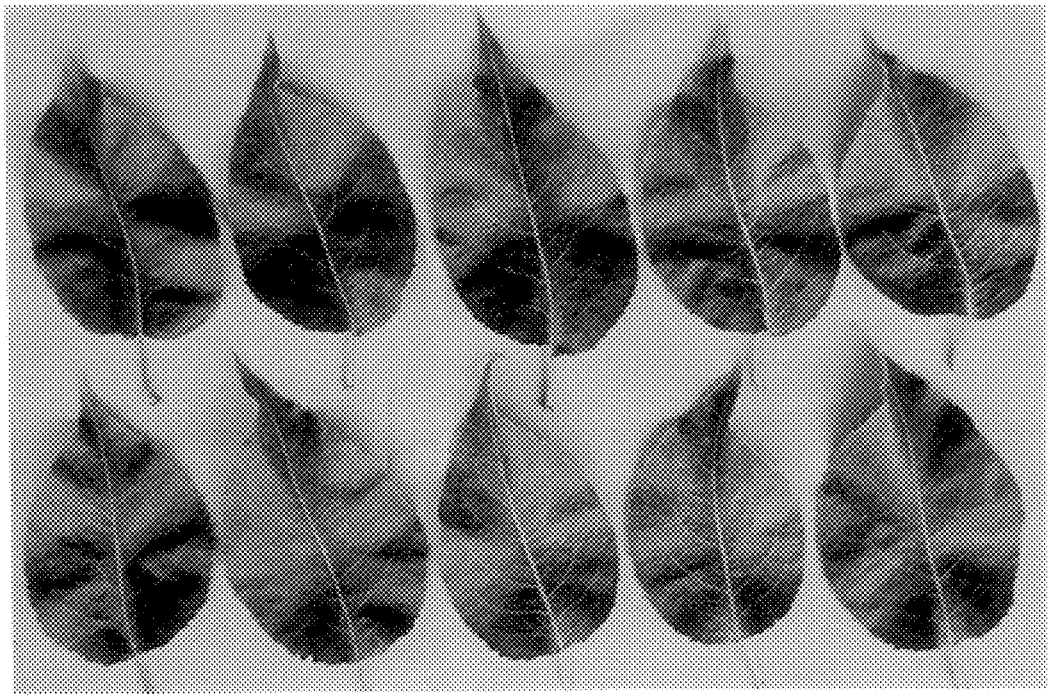
FIG. 3 is a photograph of adaxial adult leaves of the new cultivar of Japanese pear tree.
Figure 4:
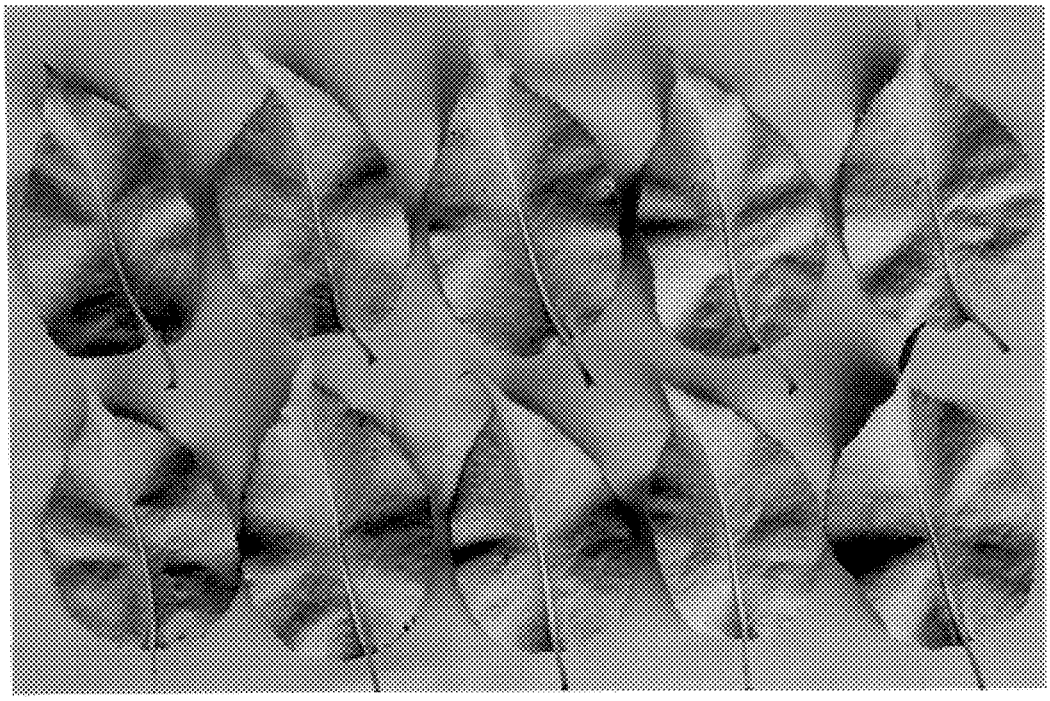
FIG. 4 is a photograph of abaxial adult leaves of the new cultivar of Japanese pear tree.
Figure 5:
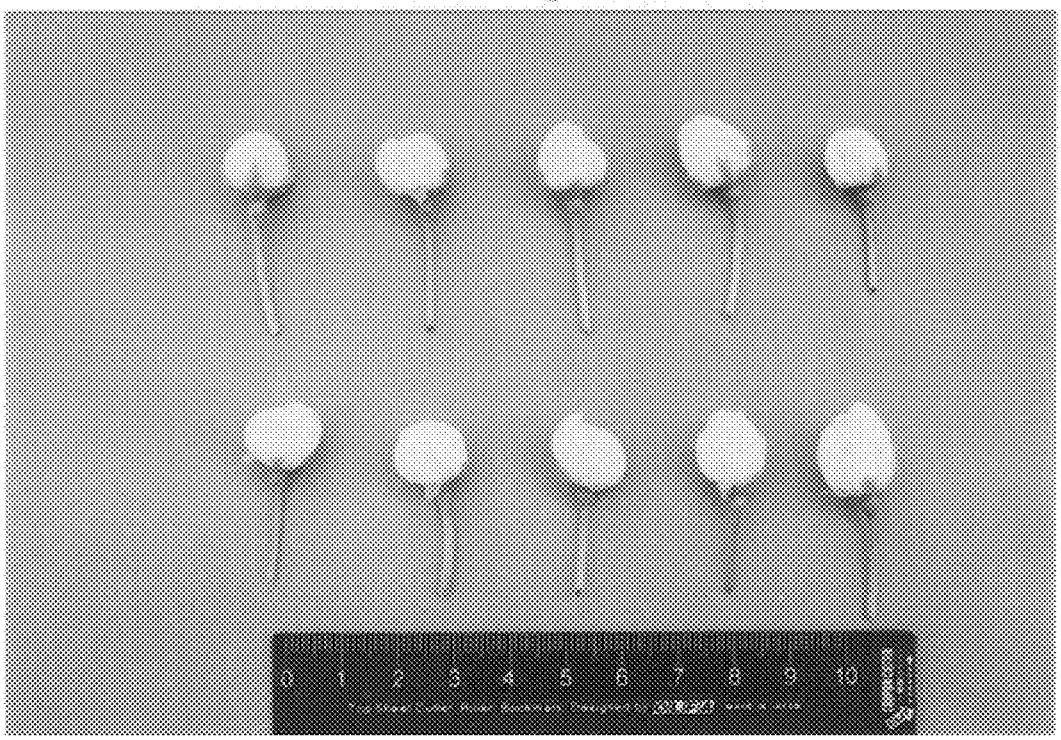
FIG. 5 is a photograph of the side of flowers in the bud stage of the new cultivar of Japanese pear tree.
Figure 6:
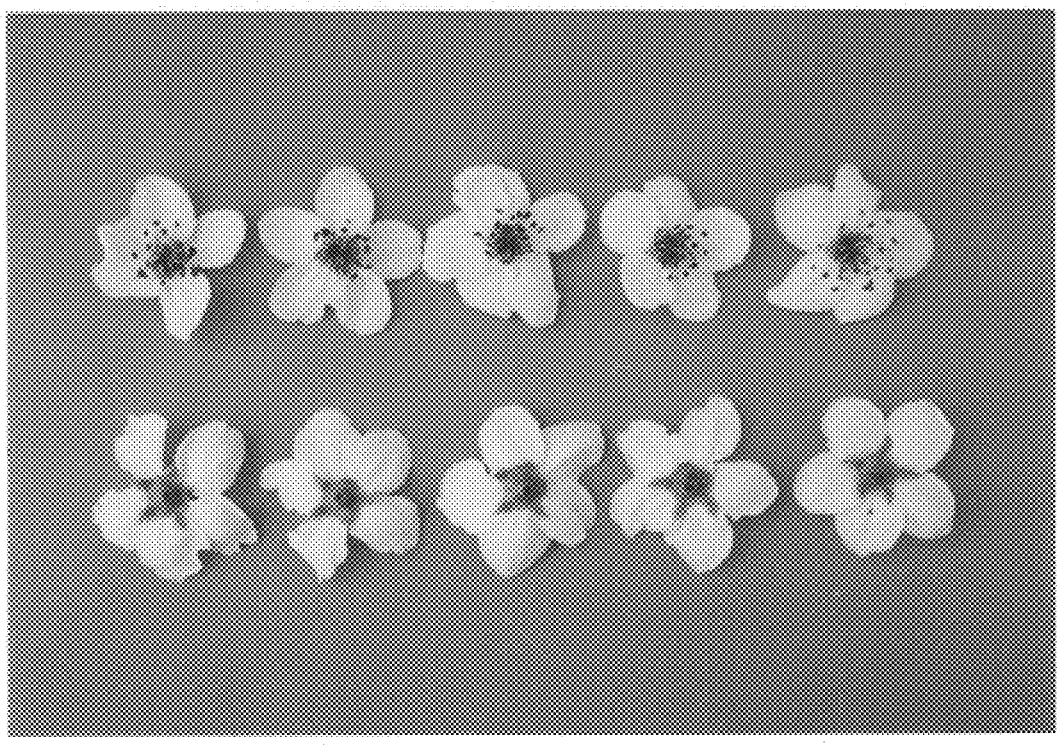
FIG. 6 is a photograph of flowers of the new cultivar of Japanese pear tree.
Figure 7:
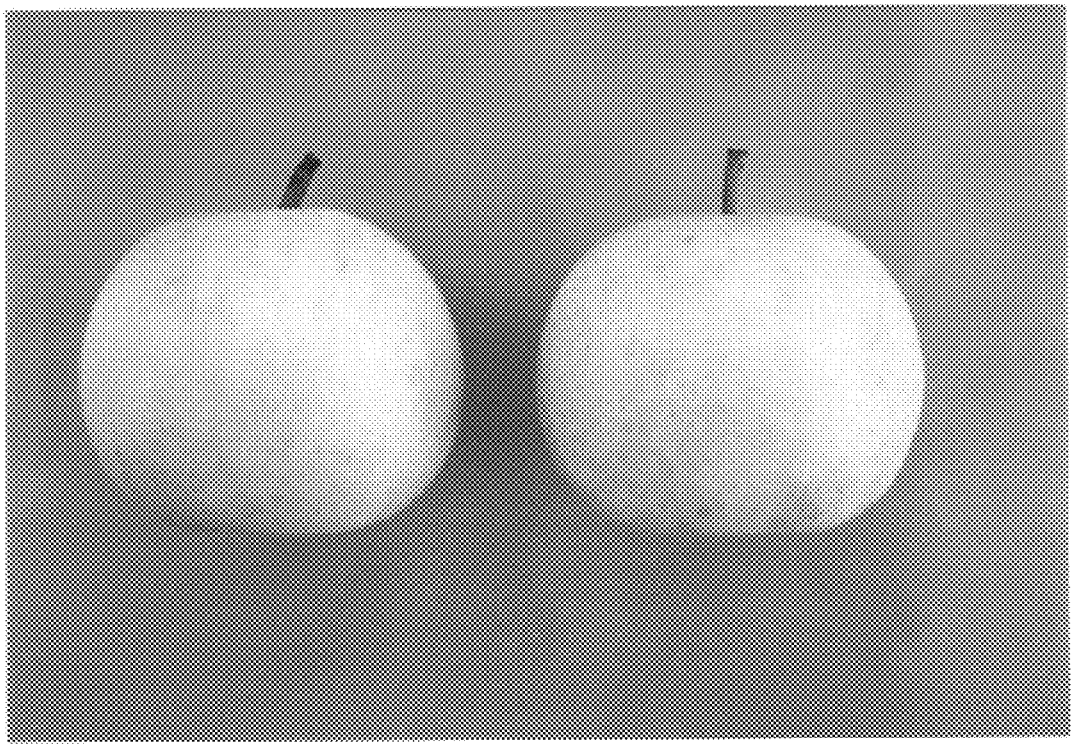
FIG. 7 is a photograph of the side views of the fruit of the new cultivar of Japanese pear tree.
Figure 8:
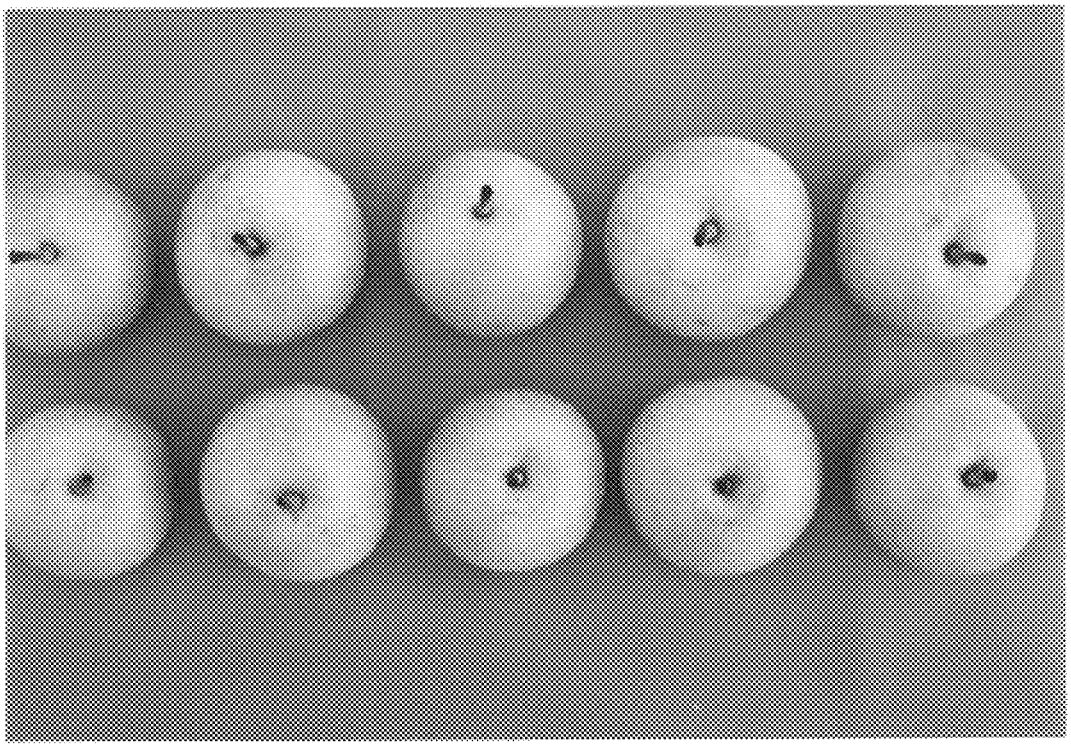
FIG. 8 is a photograph of views at the stem end of the fruit of the new cultivar of Japanese pear tree.
Figure 9:
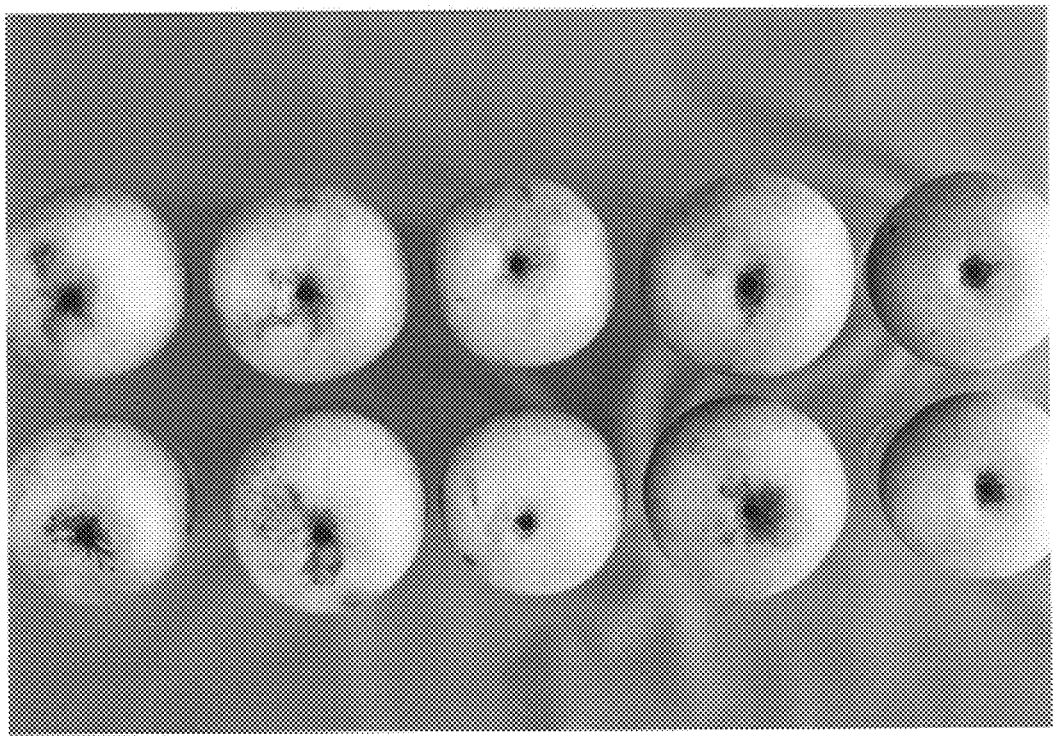
FIG. 9 is a photograph of views at the blossom end of the fruit of the new cultivar of Japanese pear tree.
Figure 10:
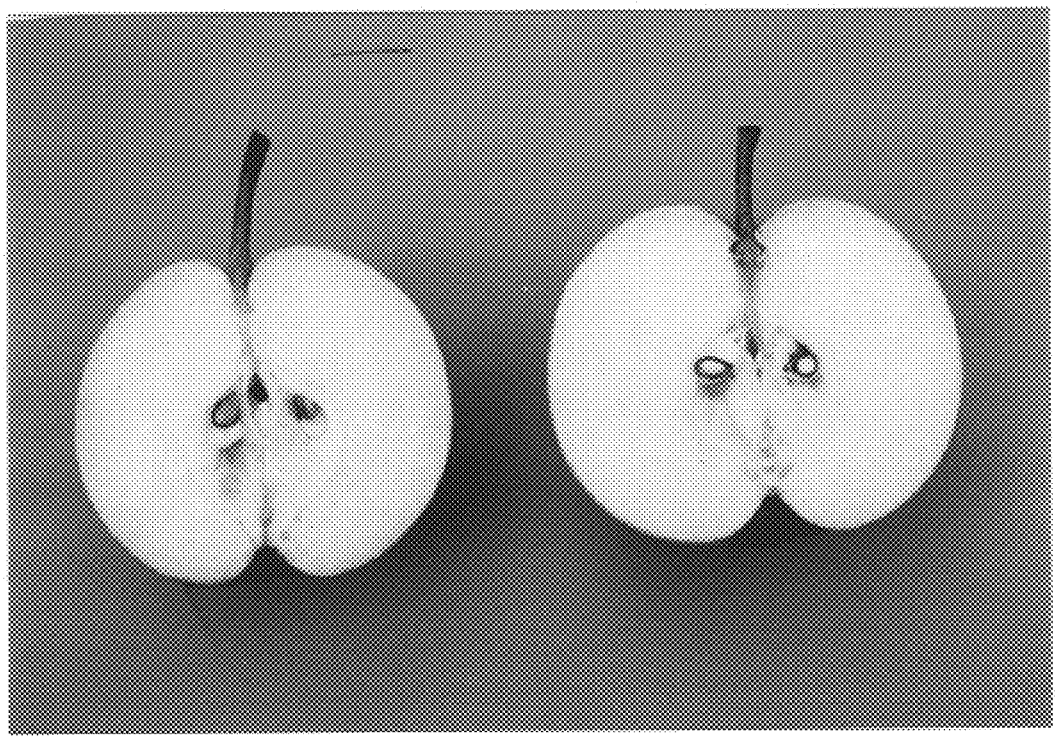
FIG. 10 is a photograph of a longitudinal-sectional view of fruits of the new cultivar of Japanese pear tree.
Figure 11:
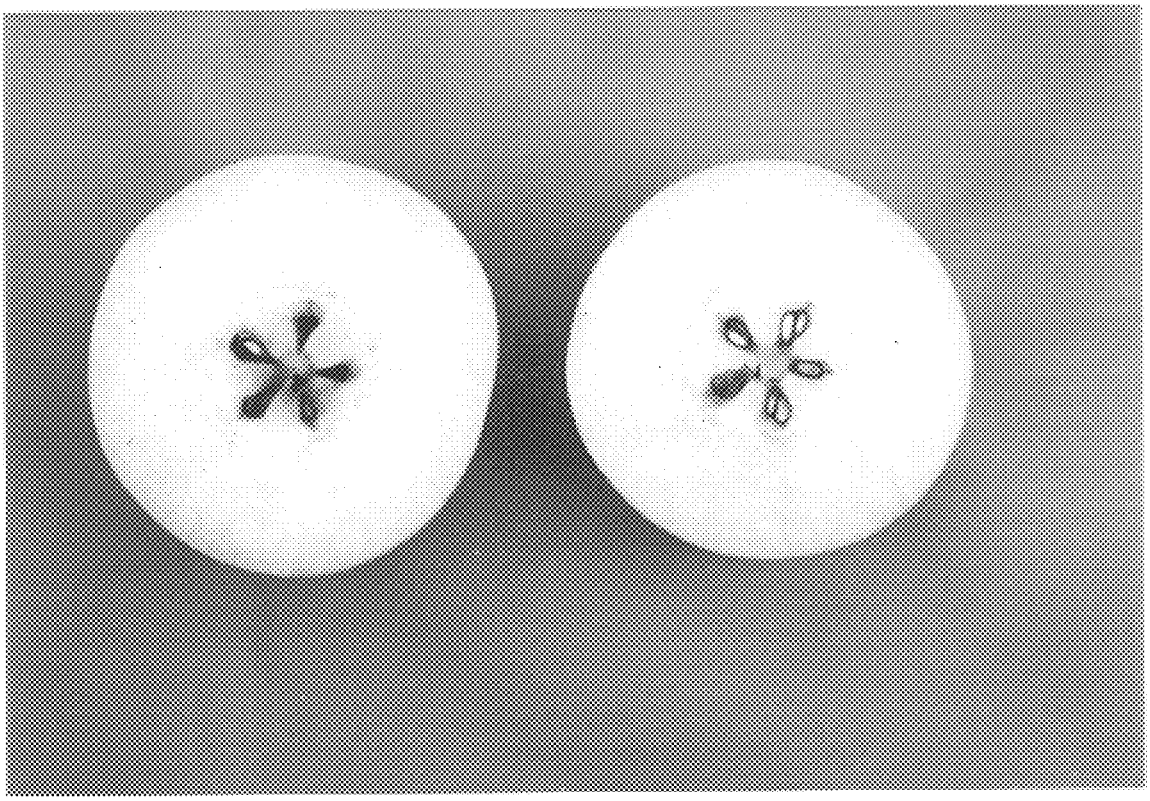
FIG. 11 is a photograph of a cross-sectional view of fruit of the new cultivar of Japanese pear tree.
Figure 12:
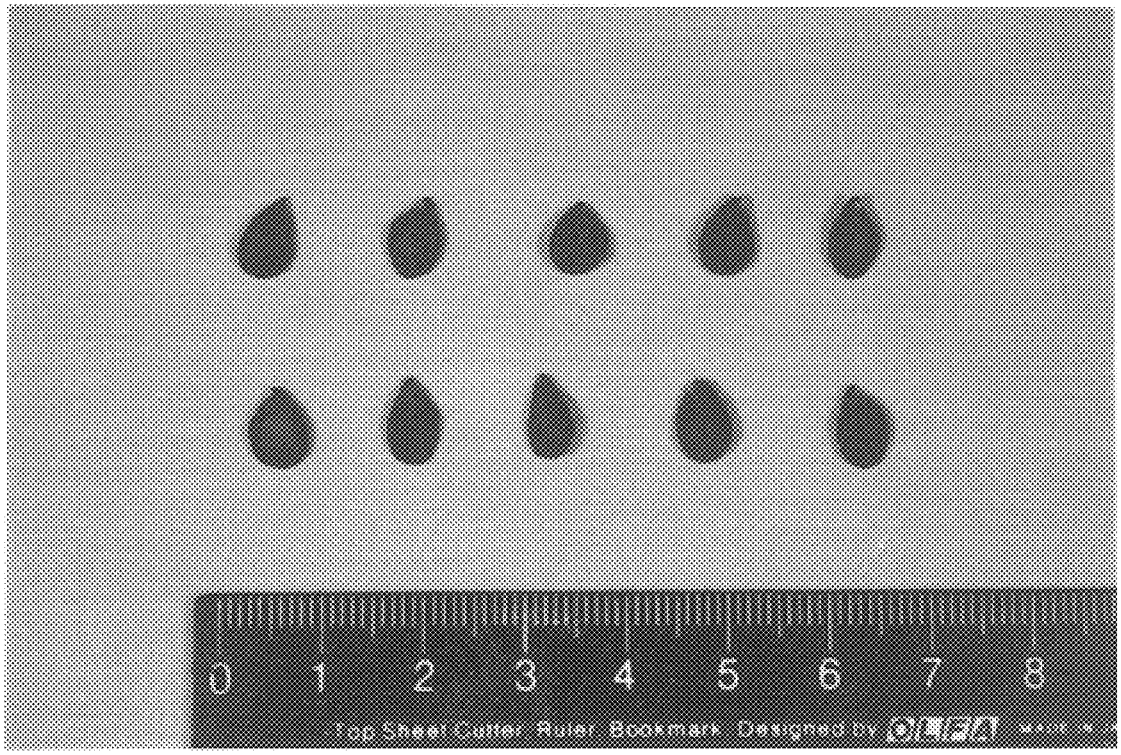
FIG. 12 is a photograph of the side views of seeds of the new cultivar of Japanese pear tree.

The characteristics of the new and distinct cultivar of Japanese pear tree 'OSA GOLD' are as follows (In the following description, the color-coding is in accordance with The Royal Horticultural Society's R.H.S. Colour Chart):

Tree:

*Vigor.*—Medium. The amount of growth of a new shoot in 1999 was an average of 110 cm.

*Spurs.*—Many. The number of spurs in 1999 averaged about 15 spurs per meter length of a branch.

*Number of axillary flower bud.*—Few.

*Time of bud break.*—Medium, around April 10th, at Ibaraki prefecture, Japan.

*Production.*—Medium productivity.

*Self-compatibility.*—High.

*Bark.*—The lenticels of the wood are medium, and density thereof is medium (the average number of lenticels is about 115 per 10 cm long branch).

Branches (Shoot):

*Length.*—Medium.

*Thickness.*—Stout, about 10 mm.

*Length of internode.*—Short, about 4 cm.

*Color.*—R.H.S. Greyed-Purple 187A.

*Density of pubescence.*—High.

*Angle between leaf bud and shoot.*—Acute.

Leaves:

*Shape.*—Ovate. The leaf margin has a serrulate shape. The leaf base is petiolate. The leaf tip shape is acuminate and the venation pattern is pinnate.

*Size.*—Medium (12.7 cm×7.5 cm).

*Color.*—Adult leaves (adaxial), R.H.S. Green 131A; adult leaves (abaxial), R.H.S. Green 138B; young leaves (adaxial), R.H.S. Red-Purple 60A; young leaves (abaxial), R.H.S. Red-Purple 60C.

*Length of petiole.*—Short, about 2.2 cm.

*Thickness of petiole.*—Medium.

*Density of pubescence of young leaves.*—High. Pubescence is shed as leaves mature.

Flowers:

*Duration of bloom.*—Approximately 10 days at Ohmiya-machi, Naka-gun, Ibaraki-ken.

*Flower number in a flower cluster.*—Slightly more than medium, 9.1 flowers per cluster on average.

*Size.*—Medium. Diameter is about 30 mm and the depth is about 5 mm.

*Color.*—Calyx (R.H.S. Green 140B); buds (R.H.S. Red-Purple 57C) early in the growing season; buds (R.H.S. White 155D) late in the growing season; petals (R.H.S. White 155D) after flowers opened.

*Shape of petals.*—Round.

*Notch at margin of petals.*—Medium.

*Number of petals.*—Slighhtly more than medium, 5.4 per flower on average.

*Color of anther.*—R.H.S. Red-Purple 64A.

*Number of stamens.*—Slightly more than medium, 25.5 on average.

*Flowering time.*—Middle of the season.

*Flowering date and full bloom stage.*—Around April 20th and April 24th at the Ibaraki prefecture, Japan. Two days earlier than 'Suisei' and the same as 'Osanijisseiki' and 'Nijisseiki'.

Fruit:

*Size.*—The average weight of the fruit is around 300 g (the average weight was 225 g in 1993, 267 g in 1994, 275 g in 1995, 303 g in 1996, 224 g in 1997, 351 g in 1998 and 290 g in 1999). The average transverse diameter of the fruit was 8.5 cm and the average axial diameter was 7.1 cm in 1999.

*Shape.*—Laterally compressed. More oblate than round, or spheroidal.

*Color of skin.*—R.H.S. Yellow 4B.

*Occurrence of russet.*—Medium.

*Calyx perpetual fruit.*—Almost all of the fruits are calyx deciduous, but some fruits are calyx perpetual.

*Size of dots on fruit skin.*—Medium.

*Density of dots on fruit skin.*—Medium.

*Color of flesh.*—R.H.S. Yellow-White 158C.

*Flesh.*—Soft and juicy. The firmness is about 5.5 lbs. according to Magness-Teller's hardness meter index.

*Size of calyx opening.*—The maximum diameter is about 2.8 cm and the deepest depth is about 0.75 cm.

*Length of stem.*—Medium.

*Thickness of stem.*—Stout.

*Color of stem.*—R.H.S. Yellow-Green 146C.

*Color of dots on fruit skin.*—R.H.S. Greyed-Yellow 162C.

*Color of core.*—R.H.S. Yellow-White 158D.

*Shape of core.*—Short conical.

*Size of core.*—Medium (the transverse core diameter was about 33.7 mm when the transverse fruit diameter was about 81.0 mm).

*Seed cells.*—medium. 5.2 cells per fruit on average.

*Size of seeds.*—Medium.

*Shape of seeds.*—Oval.

*Taste.*—Medium sweetness, the total sugar content of the fruit juice is about 11.0%, a medium acidity, pH 4.8, and no astringency.

*Bagged.*—The bagged fruit has lower occurrence of russet.

*Maturity.*—Ripening slightly early in the season, e.g., around September 15th at the Ibaraki prefecture, Japan.

*Use.*—Suitable for dessert.

*Keeping quality.*—The fruits can keep their quality about 3–4 months at a temperature of 4° C.

*Productivity.*—4.7 kg/tree, i.e. 290 g (average weight of a fruit)×162 (average numbers of fruits/tree), in 1999. However, the size of a fruit and the yield change greatly depending on degree of training, pruning and fruit thinning, and weather conditions.

*Resistance to diseases.*—The leaves, petals and young fruit were inoculated indoors with AK-toxin (produced by *Alternaria alternata* Japanese pear pathotype) or with black spot disease spores (atomizing inoculation with $5\times10^5$ spores/ml of strain 15A) for a disease resistane test (see FIGS. 13–16).

Figure 13:
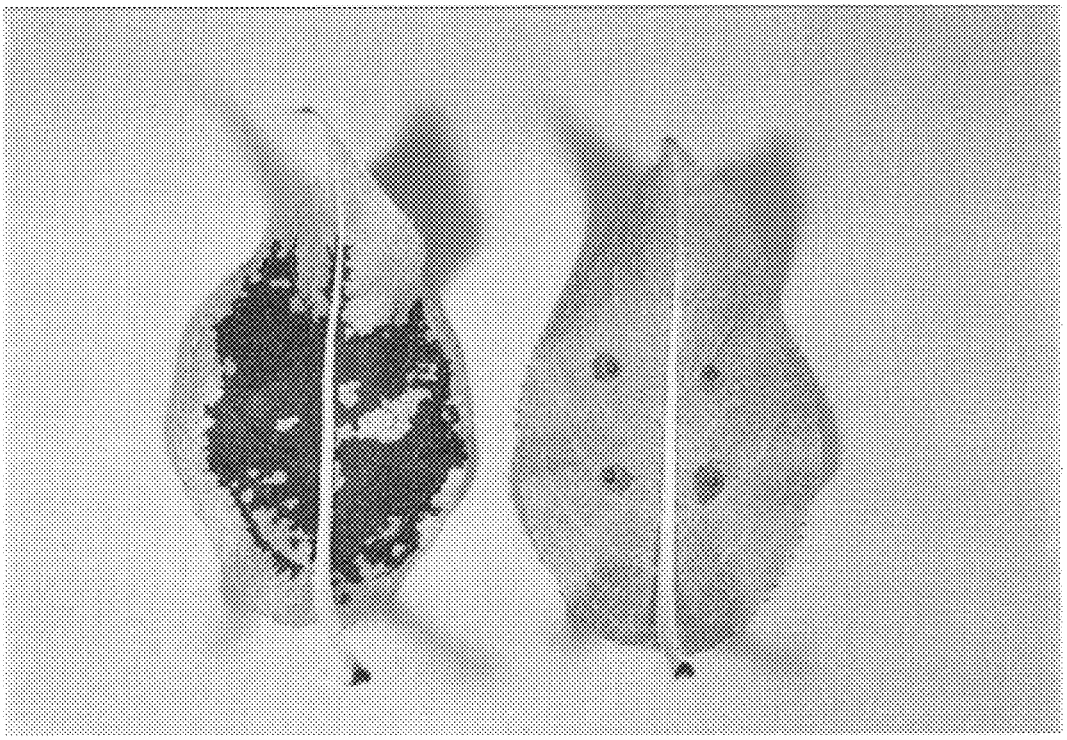
FIG. 13 is a photograph of the leaves, of 'Osanijisseki' (left) and 'Osa Gold' (right) treated with crude AK toxin (after 48 hours).
Figure 14:
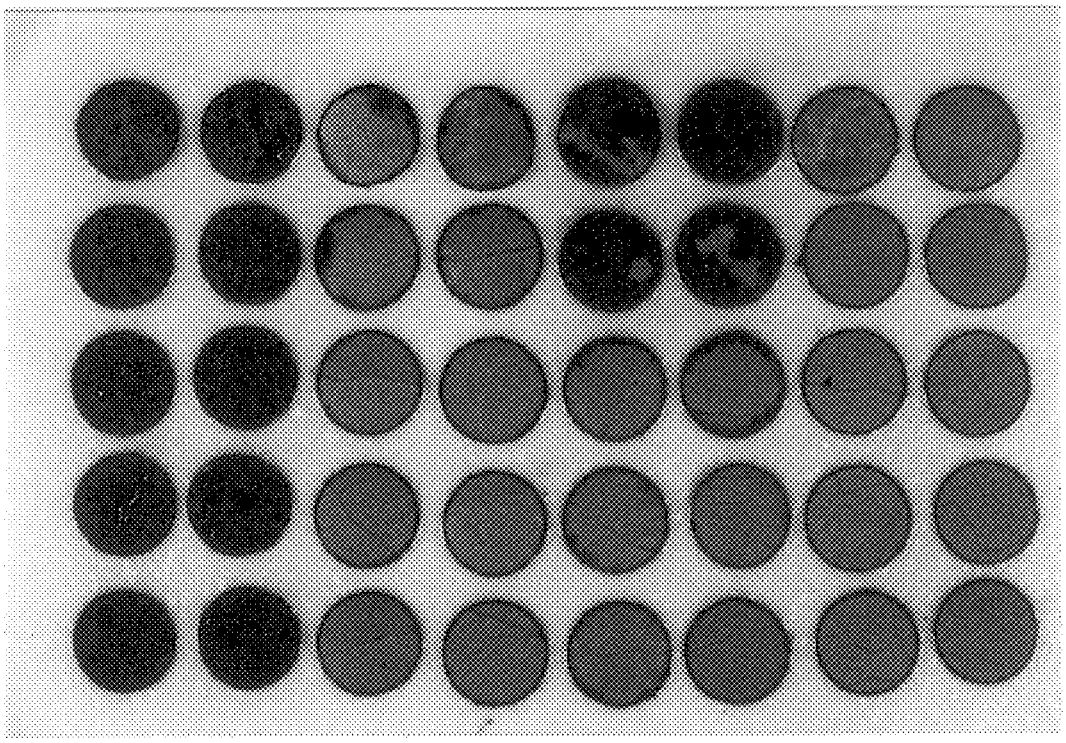
FIG. 14 is a photograph of the leaf disks of the first (the top rank) to the fifth leaves (the bottom rank) of 'Osanijisseki', 'Osa Gold', 'Gold Nijisseiki' and, 'Chojuro' (unpatented in the United States) from the left column to the right column, in pairs of lines, treated with crude AK toxin (after 48 hours).

Upon examination with AK-toxin treatment, typical symptoms of black spot disease and extensive necrosis were found all over the leaves of the original cultivar 'Osanijisseiki', while necrosis was found only on portions of the leaves of 'OSA GOLD' (FIG. 13). With toxin treatment using the leaf disks of the first leaves to the fifth leaves, treatment of the original cultivar 'Osanijisseiki' with the toxin resulted in necrosis on the whole of the leaf disks, but 'OSA GOLD' showed only slight blackening on the leaf disks from the young leaves (FIG. 14).

Figure 15:
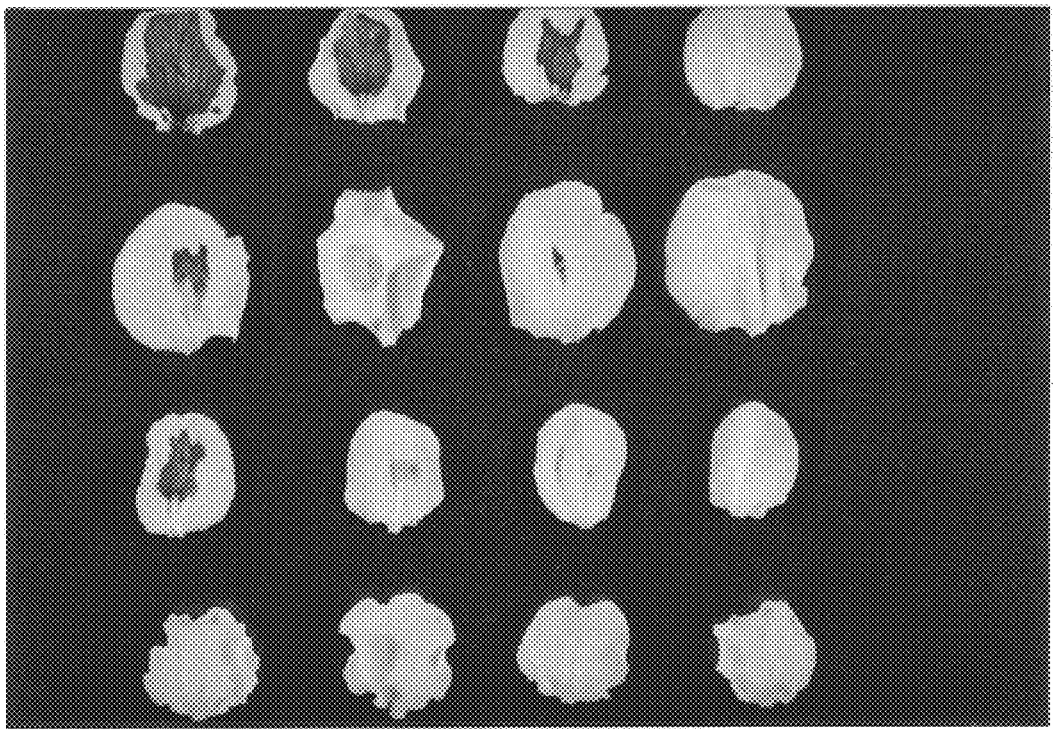
FIG. 15 is a photograph of petals of 'Osanijisseiki', 'Osa Gold', 'Gold Nijisseiki' (U.S. Plant Pat. No. 8,529) and 'Chojuro' from the top rank to bottom rank, treated with crude toxin ($10^{-5}$ M), ($10^{-6}$ M), ($10^{-7}$ M) and distilled water (as a control) from the left column to the right column.

Toxin treatment of the petals gave results similar to those for the leaves and leaf disks (FIG. 15).

Figure 16:
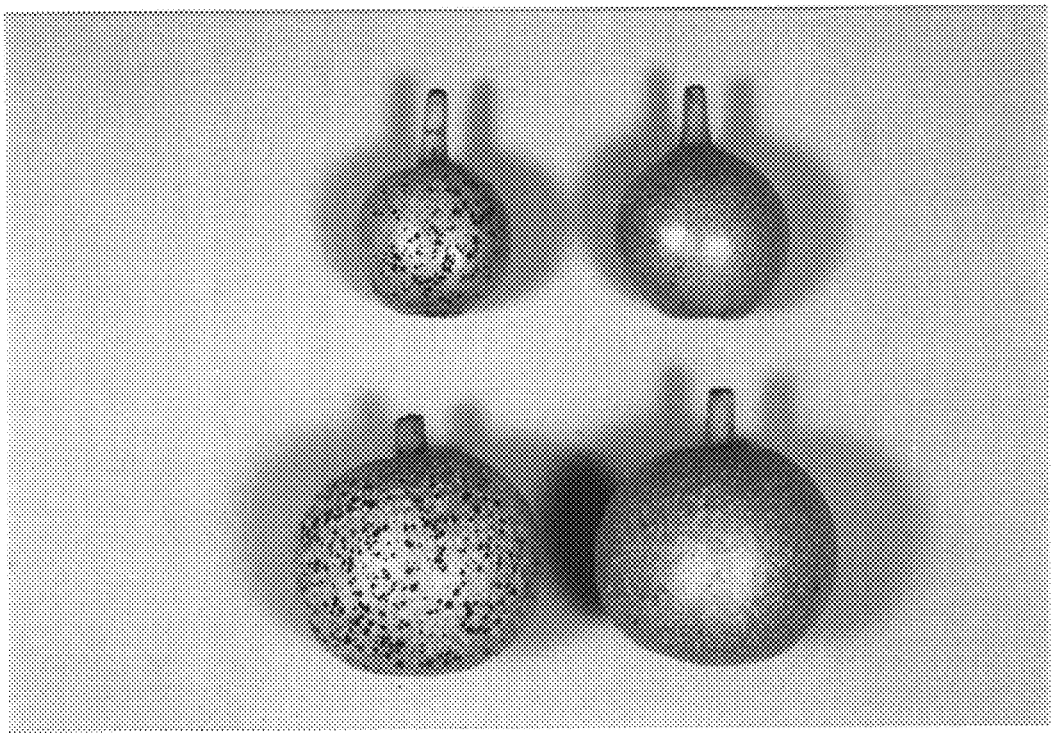
FIG. 16 is a photograph of young fruits after 30 days (the upper row) and 50 days (the lower one) after flowering of 'Osanijisseiki' (left) and 'Osa Gold' (right) after 24 hours of inoculation of $5\times10^5$ per ml spores of 15A Strain.
Figure 17:
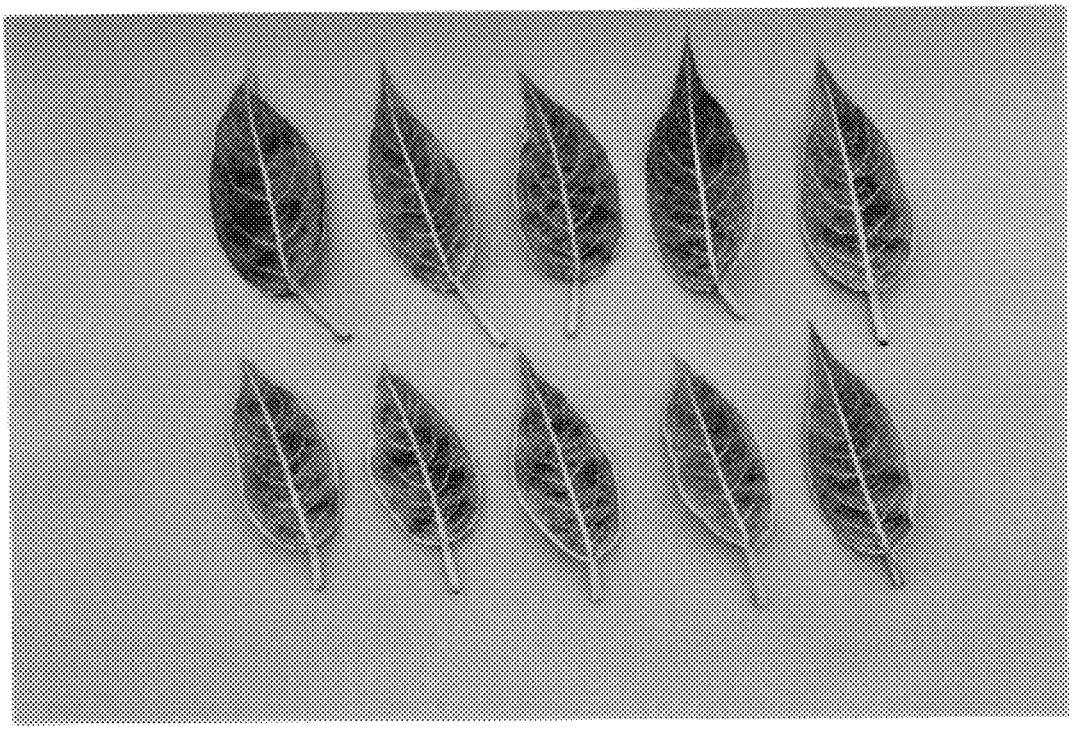
FIG. 17 is a photograph of adaxial young leaves of the new cultivar of Japanese pear tree.
Figure 18:
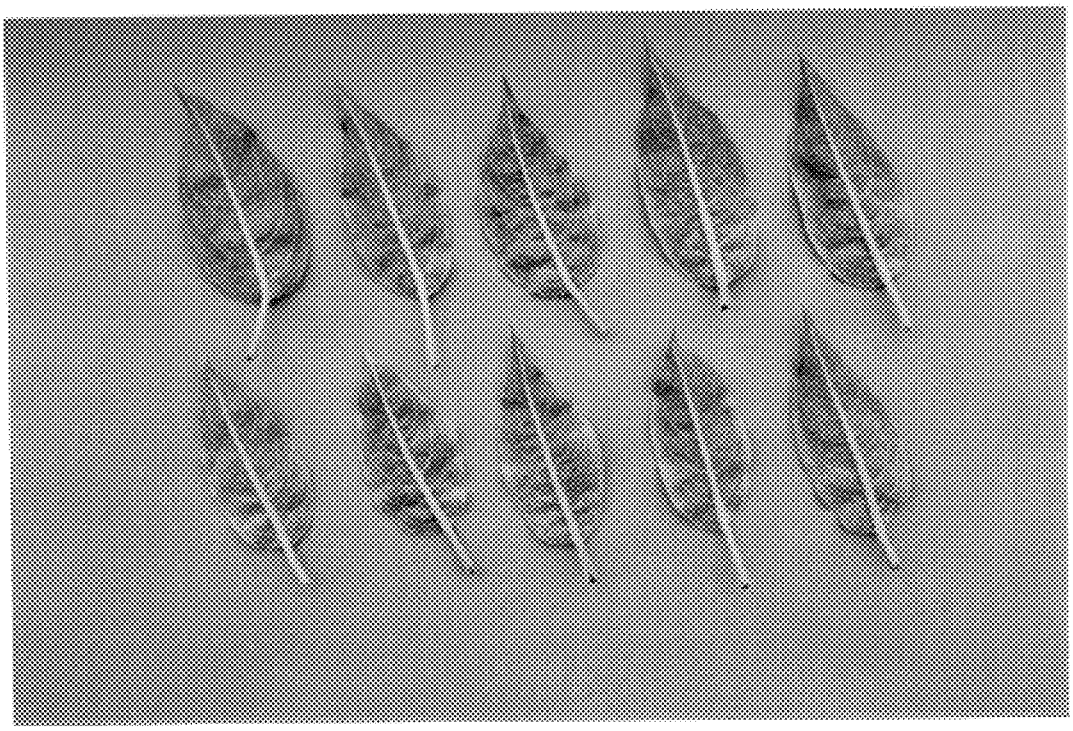
FIG. 18 is a photograph of abaxial young leaves of the new cultivar of Japanese pear tree.

In the spore inoculation test on the young fruit, widespread symptoms were found in the original cultivar 'Osanijisseiki', while only small blackened areas were found in 'OSA GOLD' (FIG. 16).

Upon observation of the extent of onset of black spot disease in field cultivation, 'OSA GOLD' was clearly stronger than the original cultivar 'Osanijisseki', as 'Osanijisseiki' exhibited severe symptoms in the current shoots and young fruit with considerable fruit abscission due to black spot disease with non-bag cultivation, while 'OSA GOLD' exhibited only slight symptoms and no fruit abscission.

Thus, the disease resistance of 'OSA GOLD' was demonstrated to be stronger than that of the original cultivar and, although it was not the complete resistance as 'Chojuro', it was a medium level of resistance similar to 'Gold Nijisseiki'.

The disease control methods used for the resistant cultivar 'Kosui' and 'Hosui' can be adequately applied as control methods.

The present tree has susceptibility to pear necrotic spot virus, and has minor susceptibility to pear scab, and no susceptibility to pear cancer and physalospora canker.

Cold resistance: Almost the same as that of other Japanese pears.
Core breakdown: Absent.
Watercore: Slightly apparent.
Fruit cracking: Absent.

The new cultivar of Japanese pear tree 'OSA GOLD' is cultivated and kept at the Institute of Radiation Breeding, National Institute of Agrobiological Resources, MAFF, Japan.

Since the new cultivar, 'OSA GOLD', has a strong resistance to black spot disease, and has substantially the same characteristics as those of the original 'Osanijisseiki', except that 'OSA GOLD' has a stronger resistance to the black spot disease, the trees of the present cultivar can be labor-savingly and easily cultivated in all the agricultural districts where 'Nijisseiki' is cultivated.

We claim:

1. A new and distinct cultivar of Japanese pear tree, substantially as herein illustrated and described.

* * * * *